United States Patent [19]

Hough

[11] Patent Number: 4,606,329

[45] Date of Patent: Aug. 19, 1986

[54] IMPLANTABLE ELECTROMAGNETIC MIDDLE-EAR BONE-CONDUCTION HEARING AID DEVICE

[75] Inventor: Jack V. D. Hough, Yukon, Okla.

[73] Assignee: Xomed, Inc., Jacksonville, Fla.

[21] Appl. No.: 736,766

[22] Filed: Jun. 17, 1985

[51] Int. Cl.$^4$ ............................................. H04R 25/00
[52] U.S. Cl. .................................... 128/1 R; 128/421; 179/107 R; 179/107 BC
[58] Field of Search ............................... 128/1 R, 421; 179/107 R, 107 E, 107 BC

[56] References Cited

U.S. PATENT DOCUMENTS

| | | |
|---|---|---|
| 2,402,392 | 6/1946 | Goldschmidt . |
| 3,209,081 | 9/1965 | Ducote et al. . |
| 3,594,514 | 7/1971 | Wingrove ............................ 128/1 R |
| 3,712,962 | 1/1973 | Epley ................................ 179/107 R |
| 3,764,748 | 10/1973 | Branch ............................... 128/1 R |
| 3,870,832 | 3/1975 | Fredrickson . |
| 4,052,754 | 10/1977 | Homsy .................................. 128/1 R |
| 4,352,960 | 10/1982 | Dormer et al. . |
| 4,357,497 | 11/1982 | Hockmair ........................ 179/107 BC |
| 4,498,461 | 2/1985 | Hakansson . |
| 4,532,930 | 8/1985 | Crosby ........................... 179/107 BC |

OTHER PUBLICATIONS

Scand Audiol 13; Mar. 1984; "Hearing Thresholds with Direct Bone Conduction Versus Conventional Bone Conduction"; by B. Hakansson, A. Tjellstrom and U. Rosenhall.

"Direct Bone Anchorage of External Hearing Aids"; by A. Tjellstrom, J. Lindstrom, O. Hallen, T. Albrektsson and P. J. Bronemark; J. Biomed Eng., vol. 5; Jan. 1983.

"Bone Conduction Speech Discrimination"; by Mendell Robinson, MD and Stephen D. Kasden, MS; Arch Otolaryngol, vol. 103, Apr. 1977.

Primary Examiner—William L. Freeh
Attorney, Agent, or Firm—Bell, Seltzer, Park & Gibson

[57] ABSTRACT

An implantable electromagnetic middle-ear bone conduction hearing aid device is disclosed which provides variability to meet a variety of pathological entities of the hearing impaired user. The device utilizes a sound processing component for converting sound into an analog electromagnetic signal and has an output transmitter adapted to be placed supercutaneously on the skull of the user for transmitting the electromagnetic signal transcutaneously. A signal receiving and transmitting component is adapted to be implanted subcutaneously in the bone of the user outside of the middle ear for receiving the transcutaneous electromagnetic signal from the sound processing component and for transmitting the electromagnetic signal subcutaneously into the middle-ear of the user. A vibration generating component is adapted to be implanted in any of the small bones of the ossicular chain in the middle-ear for receiving the subcutaneous electromagnetic signal from the signal receiving and transmitting component and for vibrating the ossicular chain in response to such electromagnetic signal to stimulate normal functioning of the inner ear to create the perception of sound in the hearing impaired user.

13 Claims, 13 Drawing Figures

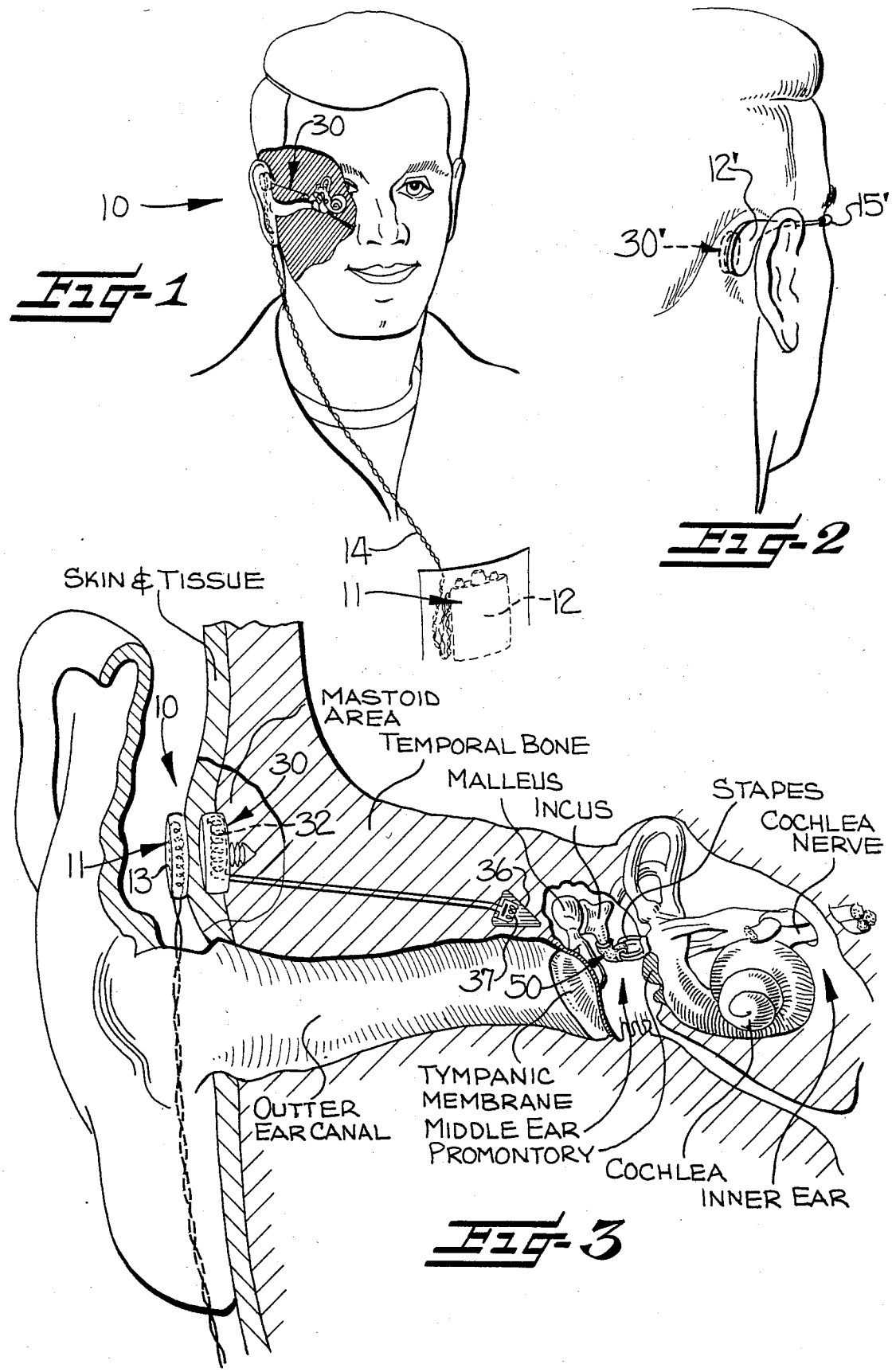

IMPLANTABLE ELECTROMAGNETIC MIDDLE-EAR BONE-CONDUCTION HEARING AID DEVICE

FIELD OF THE INVENTION

This invention relates to devices for aiding the hearing impaired and more particularly to an implantable electromagnetic middle-ear bone-conduction hearing aid device which stimulates the inner ear to create the perception of sound by conduction of vibrations through the small bones of the ossicular chain in the middle-ear of the user.

BACKGROUND OF THE INVENTION

The normal preception of sound occurs in a person when sound waves strike the tympanic membrane and cause it to vibrate. These vibrations are transmitted through the tiny bones of the ossicular chain in the middle-ear to the cochlea in the inner ear, which results in electrical impulses being transmitted through the auditory or cochlea nerve to the brain. Even if the sound conducting mechanisms of the middle-ear are functioning perfectly, a hearing loss can be experienced if the inner ear is damaged.

The more conventional hearing aid devices are of the "air conduction" type and are used to overcome a hearing loss due to inner ear damage (sensorineural loss) and/or hearing loss due to a mild impediment of the sound conducting mechanisms of the middle-ear. Such air conduction hearing aid devices work by simply amplifying the incoming sound and delivering the amplified sound signal by way of a speaker positioned in the outer ear canal. This amplified sound simply "overdrives" the ear's sound conducting mechanism. Since an air conduction hearing aid device must have some of its componentry in the outer ear canal, and since it also requires a fairly normal tympanic membrane and ossicular chain in the middle-ear, some hearing impaired persons are unable to derive any benefit from the air conduction hearing aid.

Persons who cannot benefit from an air conduction hearing aid can sometimes benefit from a "bone conduction" hearing aid. A bone conduction hearing aid works by converting the sound signal into a mechanical vibratory stimulus. Heretofore, the vibrating portion of most commercially-available hearing aids of this type has been placed against the skin, usually behind the ear, under some pressure. The vibrator transmits its vibrations through the skin and soft tissue into the bone structure of the skull. The vibration of the skull stimulates the cochlea and a sound is perceived. Such commercially available bone conduction hearing aid devices are not very popular due to several limitations. First, the devices are bulky and must be worn on a headband or a special eyeglass frame in order to keep the vibrator pressed tightly against the skull. In addition, because the vibration must be transmitted through the skin and soft tissue overlying the skull, the fidelity of sound and the efficiency of these types of hearing aid devices are poor.

Proposals have been made for improving bone conduction devices for stimulating the inner ear. One such proposal is disclosed in U.S. Pat. No. 3,290,081 in which a radio receiver is implanted underneath the skin and includes a vibration generating means which is connected to the temporal bone subcutaneously. A transmitter may be located at any remote place on the body of the user within the range of the implanted radio receiver for generating a modulated signal in response to sound received by a microphone. This modulated signal is received by the radio receiver and the vibrator is caused to vibrate in response to the modulated signal and set up vibrations within the temporal bone which in turn stimulates the inner ear to create a preception of sound. This implanted radio receiver is quite complex and includes numerous implanted electronic components including a power supply, which are susceptible to malfunction and other potential problems which could cause extreme difficulty due to the implanted nature thereof.

Another proposal relates to some experimental work conducted in Europe and described in a recent published paper wherein a direct bone conduction hearing aid device was implanted which included a bone screw implanted directly in the temporal bone subcutaneously and a post connected directly thereto. This post extends percutaneously (through the skin) to a location externally of the skin. A vibrator which creates vibrations in response to a modulated signal is connected to this post and vibrations are transmitted by the post to the bone screw and thence to the temporal bone of the skull to stimulate the inner ear and create the preception of sound. This device has distinct disadvantages, not the least of which are the likelihood of infection and the undesirability of a ceramic element extending permanently through the skin from aesthetic, psychological and comfort standpoints.

To overcome the problems presented with the above previously-proposed bone conduction hearing aid devices, a development was made, as disclosed in co-pending U.S. application Ser. No. 674,176, filed Nov. 23, 1984, and assigned to the assignee of the present application, in which a direct bone conduction hearing aid device is proposed in which the signal transmitting device is held in place without unsightly or uncomfortable external devices. This bone conduction hearing aid device includes sound processing mechanism for converting sound into an analog electromagnetic signal and having an output transmitter for transmitting the electromagnetic signal and being adapted to be placed supercutaneously on the skull of a hearing impaired person and having a first magnetic means therein. The device further includes a vibration generating mechanism adapted to be implanted subcutaneously and secured to a skull bone of the hearing impaired person and second magnetic means. This second magnetic means cooperates with the first magnetic means to hold said transmitter in position supercutaneously on the skull of the hearing impaired person, (2) receives the electromagnetic signal from said transmitter of said sound processing means, and (3) vibrates the skull bone in response to such electromagnetic signal. With this device, vibrations are generated subcutaneously in response to the analog electromagnetic signal and conducted through the bones of the skull to stimulate the inner ear to create the perception of sound in the hearing impaired person.

While this development of the aforesaid co-pending patent application performed satisfactorily for many cases, there are situations in which direct vibrations of the ossicles of the middle-ear is more desirable and may provide a more enhanced perception of sound in the hearing impaired person.

For these latter described cases, there has been proposed in U.S. Pat. No. 3,870,832 an implantable middle-ear bone-conduction hearing aid device which utilizes a sound transducer means for converting audio signals to electric signals and electromagnetic transducer means for receiving the electrical signals and converting the electrical signals into mechanical movement of the stapes bone of the ossicular chain in the inner ear. The device of this patent includes a magnet that is permanently attached to the stapes of the ossicular chain in the inner ear, an electromagnetic coil implanted in the temporal bone of the user and extending through the skin to be attached to a sound processing means outside the skin. The electromagnetic transducer receives electrical signals and transmits them by way of electrodes extending therefrom and into the middle-ear of the user and attached to the magnet secured to the stapes of the ossicular chain in the middle-ear of the user.

While this device of U.S. Pat. No. 3,870,832 directly stimulates the ossicular chain of the inner ear of the user by bone conduction, it has many disadvantages and limitations including the following. The hearing aid device requires a percutaneous element extending through the soft tissue and skin of the user behind the ear which creates the likelihood of infection from permanently open skin and bacterial invasion. It is also unacceptable from cosmetic, psychological and comfort standpoints. Secondly, this patented device utilizes electrodes which extend directly into the middle-ear of the user and are very difficult to implant surgically and open up strong possibilities of electrode fractures, insulation leaks and current leaks. Thirdly, this device only provides for a vibration generating mechanism to be attached to the head of the stapes of the ossicular chain in the middle-ear. In many cases, the promontory is too high on the inferior side to allow attachment of a vibration generating mechanism to the head of the stapes. Also, there are occasions when the facial ridge impinges on the stapes and would make such application impractical. In summary, there are many cases in which attachment of a vibration generating means to the head of the stapes in the ossicular chain will not provide the desired stimulas to the inner ear to create the required preception of sound in the hearing impaired person.

OBJECTS AND SUMMARY OF THE INVENTION

With the foregoing in mind, it is the object of the present invention to provide an implantable electromagnetic middle-ear bone-conduction hearing aid device which overcomes the deficiencies and problems heretofore encountered with bone conduction hearing aid devices and to provide such a device which is characterized by the absence of electrodes entering the middle-ear and variability to meet a variety of pathological entities of the hearing impaired user, while providing increased comfort and aesthetic appearance.

It has been found by this invention that the above object may be accomplished by providing such a hearing aid device which includes the following mechanisms. A sound processing means is provided for converting sound into an analog electromagnetic signal and includes an output transmitter adapted to be placed supercutaneously on the skull of the user for transmitting the electromagnetic signal transcutaneously. A signal receiving and transmitting means is adapted to be implanted subcutaneously in the bone of the user outside of the middle-ear for receiving the transcutaneous electromagnetic signal from the sound processing means transmitter and for transmitting said electromagnetic signal subcutaneously into the middle-ear of the user. Vibration generating means are adapted to be implanted in any of the small bones of the ossicular chain in the middle-ear for receiving the subcutaneous electromagnetic signal from said signal receiving and transmitting means and for vibrating the ossicular chain in the middle-ear in response to such electromagnetic signal to stimulate the inner ear to create the preception of sound in the hearing impaired user.

Preferably, in accordance with the present invention, the electromagnetic receiving and transmitting means includes electromagnetic signal receiving means for receiving the transcutaneous electromagnetic signal from the sound processing means transmitter and including means for attachment thereof subcutaneously to the mastoid area of the temporal bone of the user, electrodes connected at one end to the electromagnetic signal receiving means for subcutaneously conveying an electrical signal, and electromagnetic signal transmitting means connected to the other end of the electrodes and adapted to be implanted in the temporal bone of the user just outside of the middle-ear for transmitting an electromagnetic signal subcutaneously into the middle-ear of the user.

Preferably, in accordance with the present invention, the sound processing means transmitter and the signal receiving and transmitting means include magnetic means for cooperating with each other to hold the sound processing means transmitter in position supercutaneously behind the ear of the user without a percutaneous extension of the device through the skin of the user.

BRIEF DESCRIPTION OF THE DRAWINGS

Some of the features and advantages of this invention having been briefly stated, others will appear from the detailed description which follows, when taken in conjunction with the accompanying drawings, in which —

FIG. 1 is a perspective view of a hearing impaired user, with a portion of the face broken away to illustrate the relative location of the outer, middle and inner ear areas and utilizing the hearing aid device of the present invention having the sound processor component of a first form;

FIG. 2 is a partial perspective view of the user viewed from the rear of the skull and utilizing the hearing aid device having the sound processor component of a second form;

FIG. 3 is an enlarged sectional view through the ear canal of the user with the hearing aid device of this invention in position;

DETAILED DESCRIPTION OF ILLUSTRATED EMBODIMENTS

Figure 4:
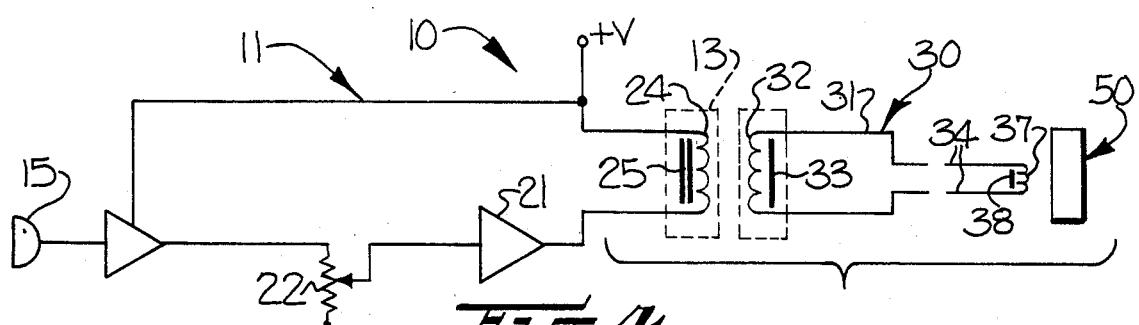
FIG. 4 is a schematic circuit diagram of the hearing aid device of this invention.
Figure 5:
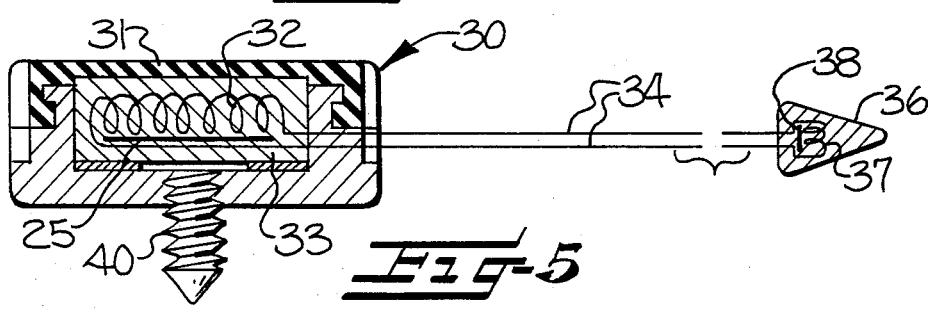
FIG. 5 is a sectional, schematic view of the electromagnetic signal receiving and transmitting component of the hearing aid device of this invention which is adapted to be implanted in the bone of the user outside of the middle-ear.

Referring now more specifically to the drawings, the implantable electromagnetic middle-ear bone-conduction hearing aid device, generally indicated at 10, is illustrated in its entirety in FIGS. 1-3 in position in the hearing impaired user. The entire ear canal, along with other anatomical areas of the user are illustrated therein and have been appropriately labeled in FIG. 3 insofar as they pertain to the present invention.

The hearing aid device 10 comprises firstly a sound processing component 11 for converting sound into an analog electromagnetic signal. As illustrated in FIG. 1, this sound processing means 11 includes a case 12 which is suitable for carrying in a pocket or being attached to the clothing of the user and an output transmitter 13 connected to the case 12 by suitable wiring 14 and adapted to be placed supercutaneously on the skull of the user, preferably behind the ear (FIG. 3) for transmitting the electromagnetic signal transcutaneously. If desired, a second transmitter 13 could be connected to the case 12 by wiring 14 and located behind the other ear to provide transmitters behind both ears of the user. Additionally, the entire sound processing means 11, including the transmitter 13, could be housed in a behind-the-ear case 12' (FIG. 2).

The sound processing means 11 may include electronic circuitry as illustrated by way of example in FIG. 4. This circuitry includes a sensitive microphone 15 for converting sound waves into electrical signals that are processed and passed to output transmitter 13 for generating at the output transmitter 13 an electromagnetic field having an amplitude proportional to the amplitude of the sound waves received by the microphone 15. Microphone 15 includes a diaphragm or membrane (not shown) which vibrates in response to the sound waves impinging thereon. The electrical signal from the microphone 15 is then amplified by a pre-amplifier 20. The amplified signal is then fed to an output amplifier 21 through a volume control 22 which provides a full or attenuated signal from the pre-amplifier 20 to the amplifier 21. The output amplifier 21 amplifies the signal and then drives the output transmitter 13. The output transmitter 13 comprises an induction coil 24 wound about a core 25.

The hearing aid device 10 further includes signal receiving and transmitting component 30 adapted to be implanted in the temporal bone of the user outside of the middle-ear (FIG. 3) for receiving the transcutaneous electromagnetic signal from the transmitter 13 of the sound processing component 11 and for transmitting an electromagnetic signal subcutaneously into the middle-ear of the user.

This signal receiving and transmitting component 30 includes an electromagnetic signal receiving means 31, preferably in the form of an induction coil 32 wound about a core 33, for receiving the transcutaneous electromagnetic signal from the sound processing component transmitter 13. Electrodes 34 are connected at one end to the signal receiving means 31 and specifically to the induction coil 32 for subcutaneously conveying an electrical signal in response to the electromagnetic signal received by the induction coil 32, 33. The signal receiving and transmitting component 30 further includes an electromagnetic signal transmitting means 36, preferably in the form of an induction coil 37 wrapped around a core 38, for receiving the electrical signal conveyed by the electrodes 34 and for transmitting an electromagnetic signal in response thereto subcutaneously into the middle-ear of the user.

As may be seen in FIG. 3, the signal receiving means 31 is adapted to be secured subcutaneously to a skull bone of the user, preferably to the mastoid area of the temporal bone by a bone screw 40. The electrodes 34 are surgically implanted to extend from the mastoid area through the temporal bone to a position near the middle-ear of the user. The electromagnetic signal transmitting means 36 is adapted to be implanted in the temporal bone just outside of the middle-ear of the user. The electrodes 34 and signal transmitting means 36 are implanted by surgically boring a passageway through the temporal bone of the user and may be covered with biocompatible material which allows the temporal bone to grow into contact with and surround the electrodes 34 and the signal transmitting means 36 for securing same in place. The induction coil 32 and core 31 of the signal receiving means 31 may be encased and covered with biocompatible and tissue tolerant materials and the bone screw 40 should be constructed of tissue tolerant material, such as titanium.

The transmitter 13 of the sound processing component 11 and the signal receiving means 31 of the signal receiving and transmitting component 30 both include magnetic means therein, preferably in the form of permanent magnets included in or forming the cores 25, 33 respectively around which the induction coils 24 and 32 are wrapped. These magnetic means cooperate with each other to hold the transmitter 13 of the sound processing component 11 in position subcutaneously on the skull of the user, preferably behind the ear, without a transcutaneous connection therebetween. Although permanent magnets are preferred, such as samariam-cobalt type, these magnetic means could take various alternative forms. For example, at least one of these magnetic means could comprise a magnet, including a permanent magnet as described above, whereas the other magnetic means could comprise magnetically attractive material, such as ferromagnetic material. Other combinations may be possible so long as the magnetic means cooperate with each other to hold the transmitter 13 of the sound processing component 11 in position supercutaneously on the skull of the hearing impaired user.

Also, although a bone screw 40 is preferred for securing the signal receiving means 31 to the skull bone of the user, other securement means such as adhesive, implanted posts, etc. could be used. Additionally, while it is preferred to secure the signal receiving means 31 of the signal receiving and transmitting component 30 to the mastoid area of the temporal bone of the hearing impaired user so as to position the transmitter 13 of the sound processing means 11 behind the ear of the user, other locations on the skull of the user are possible.

The hearing aid device 10 of this invention further includes a vibration generating component 50 adapted to be implanted in or on any of the small bones of the ossicular chain in the middle-ear of the user and includes magnetic means for receiving the subcutaneuous electromagnetic signal from the signal transmitting means 36 of the signal receiving and transmitting component 30 and for vibrating the ossicular chain or a portion thereof in response to such electromagnetic signal to stimulate normal functioning of the inner ear to create the perception of sound in the hearing impaired user.

Figure 6:
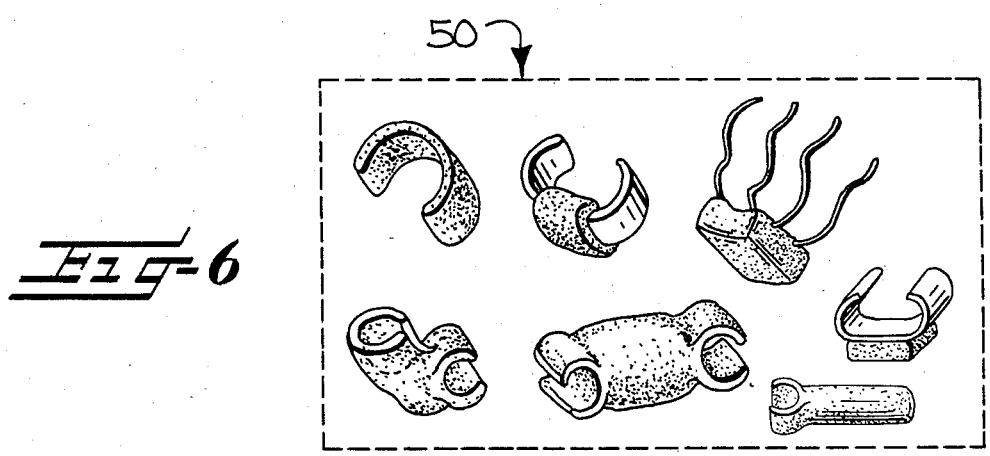
FIG. 6 is a composite view of various forms of the vibration generating component of the hearing aid device of this invention which may be implanted in any of the small bones of the ossicular chain in the middle-ear of the user.

This vibration generating component 50 is preferably in the form of a ceramic magnetic prosthesis formed of biocompatible material impregnated with rare earth magnetic particles. The vibration generating component 50 may take any desirable shape or form, such as the various forms illustrated in FIG. 6, and includes means for securement thereof to and between various small bones of the ossicular chain in the user depending upon anatomical variations, some of which are illustrated in FIGS. 7-13. The vibration generating component 50 is not connected with any electrodes extending into the middle-ear of the user, thus avoiding the danger of leaks, shorts and breaking of electrodes and eliminating the very difficult task of surgically implanting the vibration generating component 50 while being attached to electrodes.

Some of the alternative variations of implanting this vibration generating component 50 into the small bones of the ossicular chain in the middle-ear of the hearing impaired person are illustrated in FIGS. 7-13 and will be described below. However, it is to be understood that other arrangements are possible.

Figure 7:
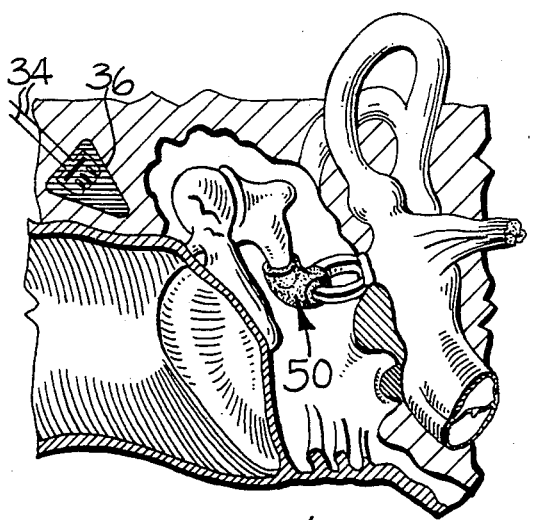
FIGS. 7–13 are partial views of the ear canal illustrating various alternative attachments of the vibration generating component in various locations in the ossicular chain of the middle-ear of the user.

Referring to FIG. 7, this is perhaps the most common application envisioned. In this application, the vibration generating means 50 is placed over the head of the stapes and under the long process of the incus in the ossicular chain in the middle-ear of the user. This application provides a vibratory insert or prosthesis in the normal ossicular chain of the middle-ear of the user.

Figure 8:
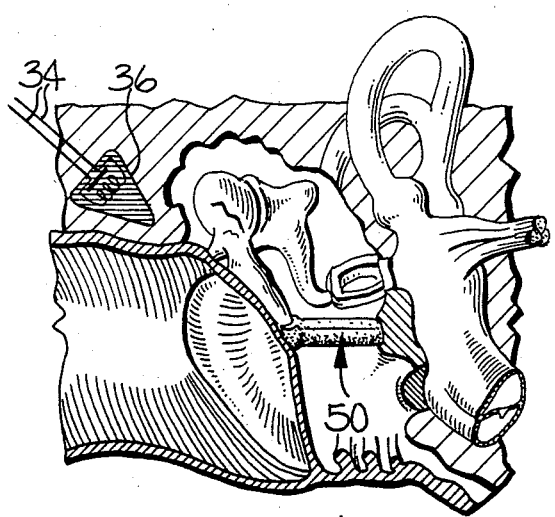

Referring now to FIG. 8, this arrangement illustrates the vibration generating means 50 secured between the promontory and the medial surface of the handle of the malleus under the tympanic membrane to provide natural vibrations of the ossicular chain duplicating the natural movement of the handle of the malleus when sound waves are imposed on the tympanic membrane of the user.

Figure 9:
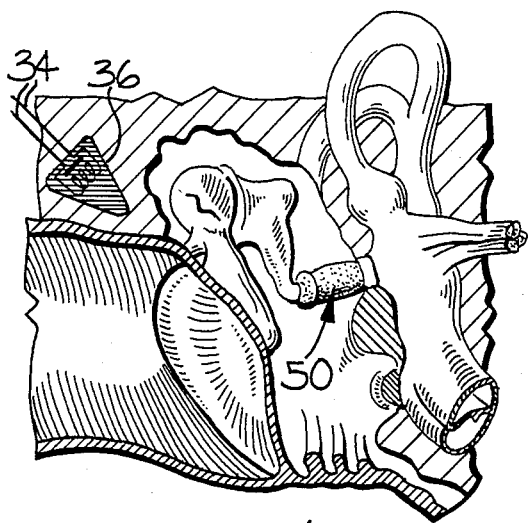

Referring next to FIG. 9, this arrangement shows the vibration generating means 50 secured between the foot plate of the stapes and the long process of the incus to function as a prosthesis when the superstructure of the stapes is missing in the user which may be caused by disease, injury or other processes.

Figure 10:
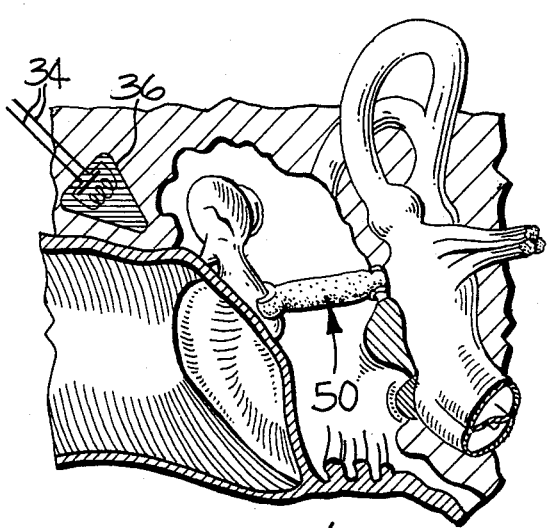

In FIG. 10, the vibration generating means 50 is shown secured between the handle of the malleus and the foot plate of the stapes to bypass the entire upper ossicular chain when the superstructure of the stapes has been damaged and the incus is no longer available for attachment in the user.

Figure 11:
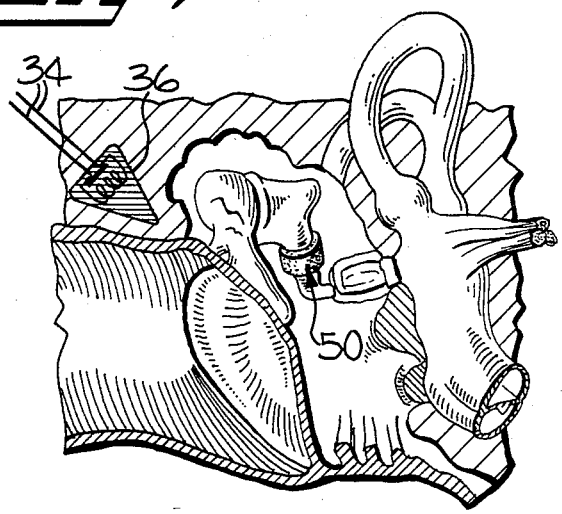

FIG. 11 illustrates the vibration generating means 50 secured to the long process of the incus which is possible in some anatomical situations, but not possible in others.

Figure 12:
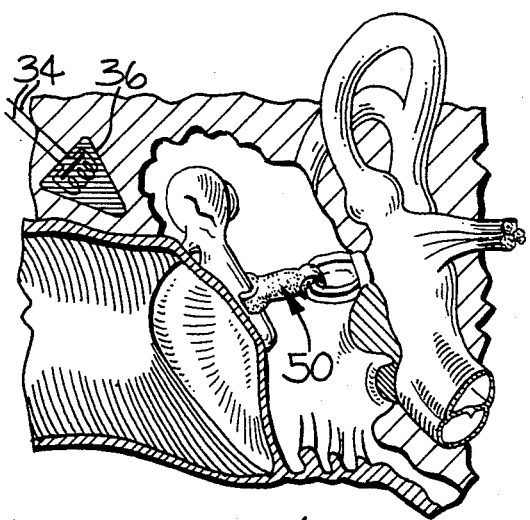

FIG. 12 illustrates the vibration generating means 50 attached between the head of the stapes and the handle of the malleus for use with ossicular chain defects producing a gap in the bridge from the tympanic membrane to the inner ear of the user. This application would be used when necrosis of the long process of the incus is present and produces a gap in the bridge from the tympanic membrane to the inner ear.

Figure 13:
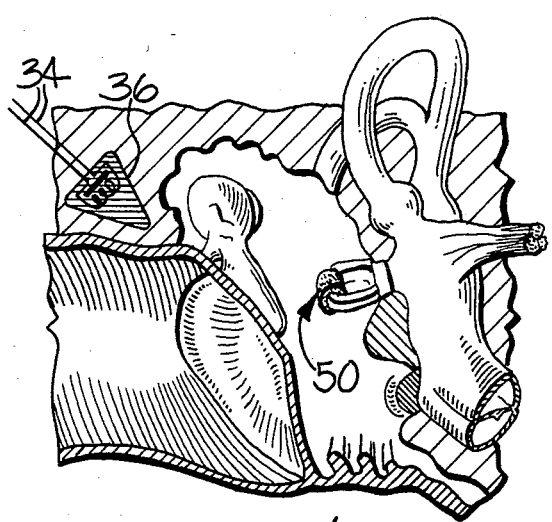

FIG. 13 illustrates the vibration generating means 50 attached to the head of the stapes in a situation similar to the application of FIG. 12, but without further attachment to the handle of the malleus, for simply vibrating the stapes when the bridge of the bones in the ossicular chain from the tympanic membrane to the inner ear contains a gap or has been disarticulated.

Thus, an implantable electromagnetic middle-ear bone-conduction hearing aid device has been provided which provides variability to meet a variety of pathological entities of the hearing impaired user, provides increased comfort and aesthetic appearance, and eliminates prior problems including electrodes entering the middle-ear of the user, etc.

In the drawings and specification, there have been disclosed typical preferred embodiments of the invention, and although specific terms are employed, they are used in a generic and descriptive sense only and not for purposes of limitation.

What is claimed is:

1. Implantable electromagnetic middle-ear bone-conduction hearing aid device characterized by the absence of electrodes entering the middle-ear and variability to meet a variety of pathological entities of the hearing impaired user; said device comprising:

sound processing means for converting sound into an electromagnetic signal and including an output transmitter adapted to be placed supercutaneously on the skull of the user for transmitting the electromagnetic signal transcutaneously;

signal receiving and transmitting means adapted to be implanted subcutaneously in the bone of the user outside of the middle-ear for receiving the transcutaneous electromagnetic signal from said sound processing means transmitter and for transmitting an electromagnetic signal subcutaneously into the middle-ear of the user; and vibration generating means adapted to be implanted in the small bones of the ossicular chain in the middle-ear for receiving the subcutaneous electromagnetic signal from said signal receiving and transmitting means and for vibrating the ossicular chain in response to such electromagnetic signal to stimulate the inner ear to create the perception of sound in the hearing impaired user.

2. Implantable electromagnetic middle-ear bone-conduction hearing aid device characterized by the absence of electrodes entering the middle-ear and variability to meet a variety of pathological entities of the hearing impaired user; said device comprising:

sound processing means for converting sound into an electromagnetic signal and including an output transmitter adapted to be placed supercutaneously behind at least one ear of the user for transmitting the electromagetic signal transcutaneously;

signal receiving and transmitting means adapted to be implanted subcutaneously and including electromagnetic signal receiving means for receiving the transcutaneous electromagnetic signal from said sound processing means transmitter and including means for attachment thereof subcutaneously to the mastoid area of the temporal bone of the user, electrodes connected at one end to said electromagnetic signal receiving means for subcutaneously conveying an electrical signal, and electromagnetic signal transmitting means connected to the other end of said electrodes and adapted to be implanted in the temporal bone of the user just outside of the middle-ear for transmitting an electromagnetic signal subcutaneously into the middle-ear of the user; and vibration generating means adapted to be implanted in any of the small bones of the ossicular chain in the middle-ear of the user and including magnetic means for receiving the subcutaneous electromagnetic signal from said signal receiving and transmitting means and for vibrating the ossicular chain in response to said electromagnetic signal to stimulate the inner ear to create the perception of sound in the hearing impaired user.

3. Implantable electromagnetic middle-ear bone-conduction hearing aid device characterized by increased comfort and aesthetic appearance, the absence of electrodes entering the middle-ear and variability to meet a variety of pathological entities of the hearing impaired user; said device comprising:

sound processing means for converting sound into an electromagnetic signal and including an output transmitter adapted to be placed supercutaneously behind at least one ear of the user for transmitting the electromagnetic signal transcutaneously and having magnetic means therein;

signal receiving and transmitting means adapted to be implanted in the temporal bone of the user outside of the middle-ear for receiving the transcutaneous electromagnetic signal from said sound processing means transmitter and for transmitting an electromagnetic signal subcutaneously into the middle-ear of the user and including a bone screw for securing at least a portion thereof subcutaneously to the mastoid area of the temporal bone of the user and magnetic means in said portion thereof for cooperating with said magnetic means of said sound processing means transmitter to hold said sound processing means transmitter in position supercutaneously behind the ear of the user without a transcutaneous connection therebetween; and vibration generating means adapted to be implanted in the small bones of the ossicular chain in the middle-ear for receiving the subcutaneous electromagnetic signal from said signal receiving and transmitting means and for vibrating the ossicular chain in response to said electromagnetic signal to stimulate the inner ear to create the preception of sound in the hearing impaired user.

4. Implantable electromagnetic middle-ear bone-conduction hearing aid device characterized by increased comfort and aesthetic appearance, the absence of electrodes entering the middle-ear and variability to meet a variety of pathological entities of the hearing impaired user; said device comprising:

sound processing means for converting sound into an electromagnetic signal and including an output transmitter adapted to be placed supercutaneously behind at least one ear of the user for transmitting the electromagnetic signal transcutaneously and having magnetic means therein;

signal receiving and transmitting means adapted to be implanted in the temporal bone of the user outside of the middle-ear and including electromagnetic signal receiving means for receiving the transcutaneous electromagnetic signal from said sound processing means transmitter and including a bone screw for securing at least a portion thereof subcutaneously to the mastoid area of the temporal bone of the user and magnetic means for cooperating with said magnetic means of said sound processing means transmitter to hold said sound processing means transmitter in position supercutaneously behind the ear of the user without a transcutaneous connection therebetween, electrodes connected at one end to said electromagnetic signal receiving means for subcutaneously conveying an electrical signal, and electromagnetic signal transmitting means connected to the other end of said electrodes and adapted to be implanted in the temporal bone of the user just outside of the middle-ear for transmitting an electromagnetic signal subcutaneously into the middle-ear of the user; and vibration generating means adapted to be implanted in the small bones of the ossicular chain in the middle-ear of the user and including magnetic means for receiving the subcutaneous electromagnetic signal from said signal receiving and transmitting means and for vibrating the ossicular chain in response to the electromagnetic signal to stimulate normal functioning of the inner ear to create the perception of sound in the hearing impaired user.

5. Hearing aid device, as set forth in claim 1, 2, 3 or 4, in which said vibration generating means includes means for securing said vibration generating means over the head of the stapes and under the long process of the incus providing a vibratory insert in the ossicular chain of the user.

6. Hearing aid device, as set forth in claim 1, 2, 3 or 4, in which said vibration generating means includes means for securing said vibration generating means between the promontory and the medial surface of the handle of the malleus under the tympanic membrane providing natural vibration of the ossicular chain duplicating the natural movement of the handle of the malleus when sound waves are imposed on the tympanic membrane of the user.

7. Hearing aid device, as set forth in claim 1, 2, 3 or 4, in which said vibration generating means includes means for securing said vibration generating means between the footplate of the stapes and the long process of the incus to function as a prosthesis when the superstructure of the stapes is missing in the user.

8. Hearing aid device, as set forth in claim 1, 2, 3 or 4, in which said vibration generating means includes means for securing said vibration generating means between the handle of the malleus and the footplate of the stapes to bypass the entire upper ossicular chain when the superstructure of the stapes has been damaged and the incus is no longer available for attachment in the user.

9. Hearing aid device, as set forth in claim 1, 2, 3 or 4, in which said vibration generating means includes means for securing said vibration generating means to the long process of the incus of the user.

10. Hearing aid device, as set forth in claim 1, 2, 3 or 4, in which said vibration generating means includes means for attaching said vibration generating means between the head of the stapes and the handle of the malleus for use with ossicular chain defects producing a gap in the bridge from the tympanic membrane to the inner ear of the user.

11. Hearing aid device, as set forth in claim 1, 2, 3 or 4, in which said vibration generating means includes means for attaching said vibration generating means to the head of the stapes for direct vibration of the stapes when a gap is present in the bridge of bones in the ossicular chain in the middle-ear of the user.

12. Hearing aid device, as set forth in claim 1, 2, 3 or 4, in which said vibration generating means comprises biocompatible material impregnated with rare earth magnetic particles to form a permanent magnet.

13. Hearing aid device, as set forth in claim 3 or 4 in which all of said magnetic means comprise permanent magnets.

* * * * *